United States Patent
VanWiggeren et al.

(10) Patent No.: US 7,027,676 B2
(45) Date of Patent: Apr. 11, 2006

(54) OPTICAL PHASE MEASUREMENT OF TARGET

(75) Inventors: Gregory D. VanWiggeren, San Jose, CA (US); Daniel B. Roitman, Menlo Park, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 34 days.

(21) Appl. No.: 10/795,917

(22) Filed: Mar. 8, 2004

(65) Prior Publication Data

US 2005/0194523 A1    Sep. 8, 2005

(51) Int. Cl.
  G02B 6/00    (2006.01)
  G02B 6/12    (2006.01)
  G01N 21/00   (2006.01)

(52) U.S. Cl. ............................. 385/14; 385/11; 385/12; 356/433; 356/432

(58) Field of Classification Search ................ 356/925, 356/432, 433; 398/52, 53, 65; 385/11–12, 385/14
See application file for complete search history.

(56) References Cited

U.S. PATENT DOCUMENTS

| | | | | |
|---|---|---|---|---|
| 5,912,740 A * | 6/1999 | Zare et al. | ................... | 356/437 |
| 6,330,064 B1 * | 12/2001 | Rieder | ........................ | 356/481 |
| 6,441,959 B1 * | 8/2002 | Yang et al. | ................. | 359/495 |
| 6,466,322 B1 * | 10/2002 | Paldus et al. | ................ | 356/437 |
| 6,512,588 B1 * | 1/2003 | Hill | ............................ | 356/510 |
| 6,515,467 B1 * | 2/2003 | Bosselmann et al. | ......... | 324/96 |
| 6,801,320 B1 * | 10/2004 | Szafraniec | ................... | 356/484 |
| 6,801,689 B1 * | 10/2004 | Sweetser et al. | .............. | 385/37 |
| 6,859,280 B1 * | 2/2005 | Kempen | ..................... | 356/369 |
| 2005/0048599 A1 * | 3/2005 | Goldberg et al. | ............. | 435/34 |
| 2005/0052655 A1 * | 3/2005 | Jones et al. | ................. | 356/491 |

OTHER PUBLICATIONS

Dennis Derickson, Editor, "Fiber Optic Test And Measurement", ISBN 0-13-534330-5, pp. 42-44.

S. G. Nelson, K. S. Johnston, S. S. Yee, "High Sensitivity Surface Plasmon Resonance Sensor Based On Phase Detection", Sensors And Actuators B 35-36 (1996); pp. 187-191.

(Continued)

*Primary Examiner*—Brian Healy
*Assistant Examiner*—Charlie Peng
(74) *Attorney, Agent, or Firm*—John L. Imperato (57) ABSTRACT

Optical phase detection includes generating a first lightwave having a first polarization and a second lightwave having a polarization that is offset from the first polarization, and imposing a relative delay between the first and second lightwaves. The relative delay causes a frequency offset between the lightwaves as wavelength is tuned over a designated wavelength range. Directing the first and second lightwaves to a target provides a third lightwave and a fourth lightwave. A polarization component of the third lightwave and a polarization component of the fourth lightwave are detected to provide a detected signal at the frequency offset. The optical phase detection then includes extracting a phase difference, induced by the target, between the polarization components of the third and the fourth lightwaves.

20 Claims, 9 Drawing Sheets

OTHER PUBLICATIONS

Yu Xinglong, Zhao Lequn, Jiang Hong, Wang Haojuan, Yin Chunyong, Zhu Shenggeng, "Immunosensor Based On Optical Heterodyne Phase Detection", Sensors And Actuators B 76 (2001); pp. 199-202.

Kun-Huang Chen, Cheng-Chih Hsu, Der-Chin Su, "Measurement Of Wavelength Shift By Using Surface Plasmon Resonance Heterodyne Interferometry", Optics Communications 209 (2002); pp. 167-172.

John Markus, "Modern Electronic Circuits Reference Manual", McGraw-Hill, Inc., ISBN 0-07-040466-1, p. 699.

Wen-Chuan Kuo, Chien Chou, Hsieh-Ting Wu, "Optical Heterodyne Surface-Plasmon Resonance Biosensor", Aug. 1, 2003 / vol. 28, No. 15 / Optics Letters; pp. 1329-1331.

A. N. Grigorenko, P. I. Nikitin, A. V. Kabashin, "Phase Jumps And Interferometric Surface Plasmon Resonance Imaging", Applied Physics Letters, vol. 75, No. 25, Dec. 20, 1999; pp. 3917-3919.

A. V. Kabashin, V. E. Kochergin, A. A. Beloglazov, P. I. Nikitin, "Phase-Polarization Contrast For Surface Plasmon Resonance Biosensors", Biosensors & Bioelectronics 13 (1998); pp. 1263-1269.

Gregory D. VanWiggeren, Ali R. Montamedi, Douglas M. Baney, "Single-Scan Interometric Component Analyzer", IEEE Photonics Technology Letters, vol., 15, No. 2, Feb. 2003, pp. 263-265.

Yu Xinglong, Wang Dingxin, Yan Zibo, "Simulation And Analysis Of-Surface Plasmon Resonance Biosensor Based On Phase Detection", Science Direct; pp. 285-290.

Gregory D. VfanWiggeren, Douglas M. Baney, "Swept Wavelength Interferometric Analysis Of Multiport Components", IEEE Photonics Technology Letters, vol. 15, No. 9, Sep. 2003, pp. 1267-1269.

* cited by examiner

OPTICAL PHASE MEASUREMENT OF TARGET

BACKGROUND OF THE INVENTION

Surface Plasmon Resonance (SPR) relates to optical excitation of a surface plasmon wave along an interface between a conductive film and an adjacent dielectric. At resonance, energy from an incident optical signal is coupled into the surface plasmon wave, resulting in a decrease in the intensity of the optical signal that is reflected from the conductive film at the optical wavelength at which the resonance occurs. A phase transition in the reflected optical signal also occurs at the resonant optical wavelength. The phase of the reflected optical signal at the resonant optical wavelength is sensitive to changes in the refractive index of the dielectric that is adjacent to the conductive film, due to an evanescent tail associated with the surface plasmon wave that extends into the dielectric. This phase sensitivity to refractive index enables the dielectric to be used as a sensing medium. For example, where the dielectric includes a biochemical sample, changes in the refractive index can be used to indicate biochemical conditions or processes in the biochemical sample.

Due to the sensitivity of phase transitions in the reflected optical signal to changes in refractive index of the dielectric or sensing medium, phase measurements based on SPR have been exploited as an analytic tool for biochemical sensing. For example, *Immunosensor based on optical heterodyne phase detection*, Sensors and Actuators B, vol. 76, Xinglong Yu, et al., (2003), p. 199–202, reports interferometry, optical heterodyning and other techniques to detect phase changes corresponding to smaller than micro-unit changes in refractive index that are linked to association/dissociation of antibodies and a protein in a biochemical sample.

There is a continuing need for phase detection schemes to further increase the sensitivity with which changes in refractive indices can be detected. In addition, there is a need for phase detection schemes based on SPR that are scalable for compatibility with analytical systems that include arrays of samples for biochemical sensing.

SUMMARY OF THE INVENTION

According to the embodiments of the present invention, optical phase detection includes generating a first lightwave having a first polarization and a second lightwave having a polarization that is offset from the first polarization, and imposing a relative delay between the first and second lightwaves. The imposed delay causes a frequency offset as the wavelength of the lightwaves is tuned over a designated wavelength range.

The lightwaves are directed to a target that provides a third lightwave and a fourth lightwave in response to the first and second lightwaves. A polarization component of the third lightwave and a polarization component of the fourth lightwave are detected to provide a detected signal at the frequency offset. The optical phase detection then includes extracting a phase difference, induced by the target, between the polarization components of the third and the fourth lightwaves. According to alternative embodiments of the present invention, scaling of the optical phase detection enables simultaneous or sequential detection of SPR-induced phase shifts from an array of targets.

DETAILED DESCRIPTION OF THE EMBODIMENTS

Figure 1:
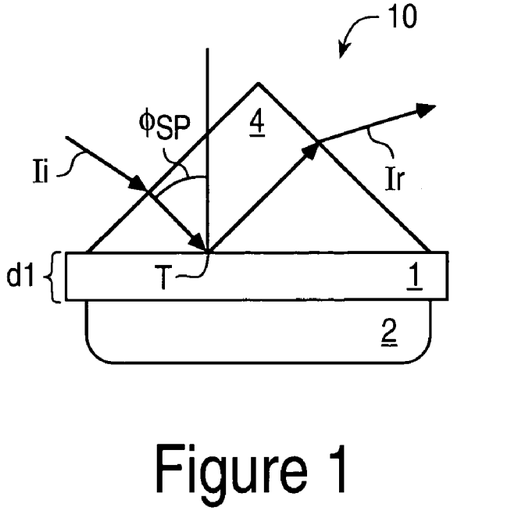
FIG. 1 shows a conventional configuration for a SPR transducer.

FIG. 1 shows a conventional SPR transducer 10, known as the Kretchmann configuration. The SPR transducer 10 includes a conductive film 1 that is adjacent to a dielectric 2. However, in some applications of the SPR transducer 10 the dielectric 2 is a sensing medium, and a linker layer (not shown) is interposed between the conductive film 1 and the dielectric 2 to provide a site for bio-molecular receptors to attach. For clarity, the conductive film 1 in FIG. 1 is shown adjacent to the dielectric 2 without the linker layer. A prism 4 is positioned adjacent to a side of the conductive film 1 that is opposite the dielectric 2. The Kretchmann configuration of the SPR transducer 10 is described in a variety of references, including *Simulation and Analysis of Surface Plasmon Resonance Biosensor Based on Phase Detection*, Sensors and Actuators B vol. 91, Xinglong Yu et al. (2003), p285–290.

In a typical application of the SPR transducer 10, the conductive film 1 is a gold layer having an appropriate thickness d1 for an incident optical signal Ii at a designated incident angle $\phi_{SP}$ and wavelength to excite a surface plasmon wave, or surface plasmon, along the conductive film 1. Associated with the surface plasmon is an evanescent tail (not shown) that penetrates into the dielectric 2 adjacent to the conductive film 1. The energy of the incident optical signal Ii that is not coupled into the surface plasmon is reflected at the conductive film 1 and results in a reflected optical signal Ir.

Figure 2:
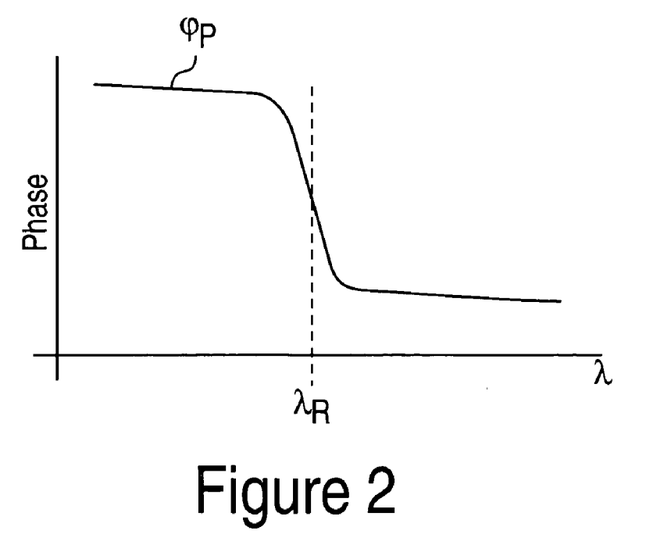
FIG. 2 shows an example phase versus wavelength for the configuration of FIG. 1.

FIG. 2 shows an exemplary phase contour of the reflected optical signal Ir in the context of the SPR transducer 10 of FIG. 1, resulting from the incident optical signal Ii impinging on a target T on the conductive film 1. The phase is indicated versus wavelength λ in the vicinity of the wavelength $\lambda_R$ at which the incident optical signal Ii couples to the surface plasmon. This wavelength $\lambda_R$ is the optical wavelength of the SPR (surface plasmon resonance), and is hereafter referred to as the resonant wavelength $\lambda_R$. FIG. 2 indicates that the phase of the reflected optical signal Ir is highly sensitive to the wavelength λ of the incident optical signal $I_1$ in the vicinity of the resonant wavelength $\lambda_R$. The resonant wavelength $\lambda_R$ in turn, is highly sensitive to changes in refractive index $n_S$ of the dielectric 2 due to the evanescent tail that penetrates the dielectric 2. Detecting phase of the reflected optical signal Ir enables changes in refractive index $n_s$ of the dielectric 2 to be detected.

Figure 3:
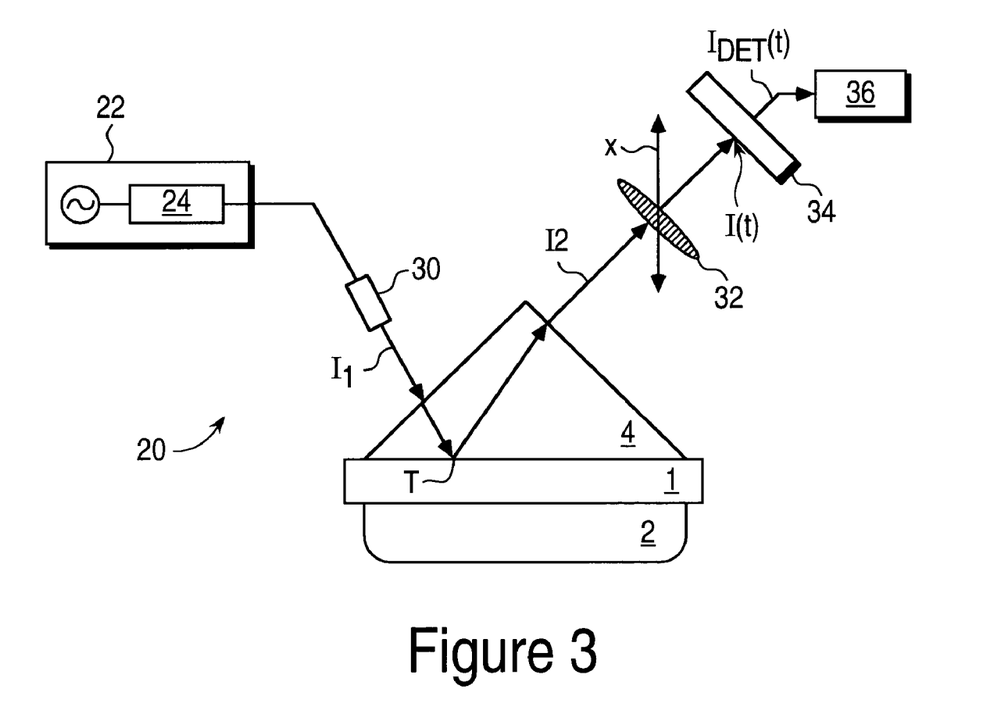
FIG. 3 shows an optical phase detector according to embodiments of the present invention.

An optical phase detector 20 according to embodiments of the present invention is shown in FIG. 3. The optical phase detector 20 includes a tunable optical source 22 that generates an optical signal $I_1$. The optical signal $I_1$ includes a first lightwave having offset a first polarization and a second lightwave having a second polarization that is offset from the first polarization. In a typical example, the offset polarizations of the first and second lightwaves are the conventional polarizations p, s. For the purpose of illustration, the lightwave having the p polarization is referred to as the lightwave p and the lightwave having the s polarization is referred to as the lightwave s.

The tunable optical source 22 includes a delay element 24 that induces a relative delay $\tau$ between the lightwaves p, s of the optical signal $I_1$. This induced delay $\tau$ results in a frequency offset $\gamma\tau$ between the lightwave p and the lightwave s as the wavelength $\lambda$ of the tunable optical source 22 is tuned or swept at a rate $\gamma$ over a wavelength range between $\lambda_1$ and $\lambda_2$.

Figure 4A:
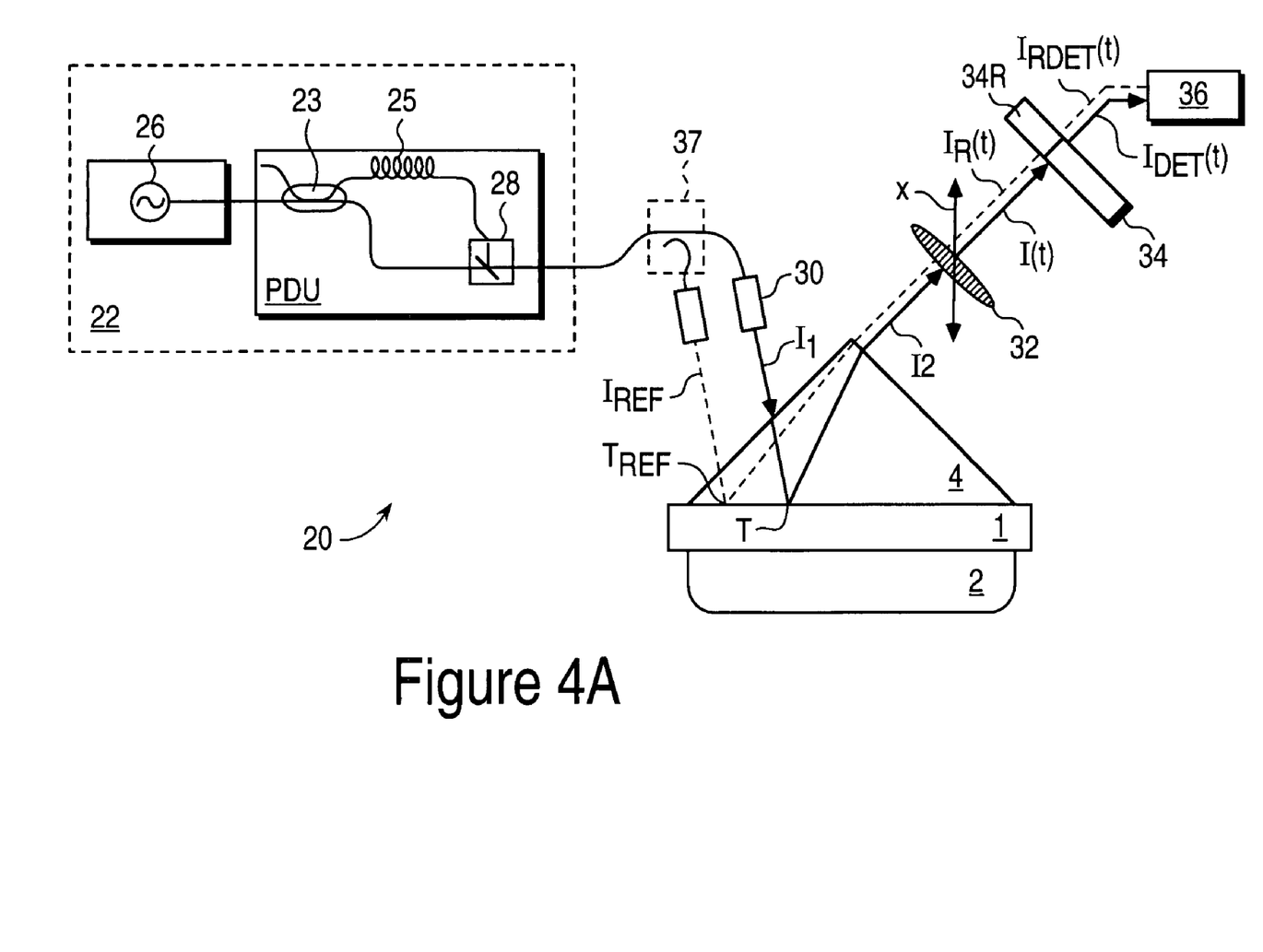
FIGS. 4A–4B show exemplary implementations of the optical phase detector of FIG. 3.

FIG. 4A shows an embodiment of the present invention wherein the tunable optical source 22 includes a tunable laser 26, cascaded with a polarization delay unit PDU. The tunable laser 26 can be swept over the wavelength range between $\lambda_1$ and $\lambda_2$. The wavelength range between $\lambda_1$ and $\lambda_2$ is sufficiently wide to accommodate shifts in the resonant wavelength $\lambda_R$ that result from corresponding shifts in the refractive index $n_s$ of the dielectric 2. In one example, the tunable laser 26 is an AGILENT TECHNOLOGIES, INC. model 81680B that can be tuned with a linear ramp within a wavelength range $\lambda_1$–$\lambda_2$ of at least 1492–1640 nanometers. The polarization delay unit PDU includes a polarization maintaining fiber coupler 23 that splits an optical signal provided by the tunable laser 26 into a first branch and a second branch. One of the branches, for example the first branch, includes a length of optical fiber 25 to induce the relative delay $\tau$ between the light in the first branch and the second branch. The first branch and the second branch are then coupled to a polarizing beam combiner 28 that transmits to a collimator 30 light from the first branch having one polarization, such as the polarization p, and light from the second branch having an offset polarization, such as the polarization s. The polarizing beam combiner 28 provides the lightwaves p, s of the optical signal $I_1$.

Figure 4B:
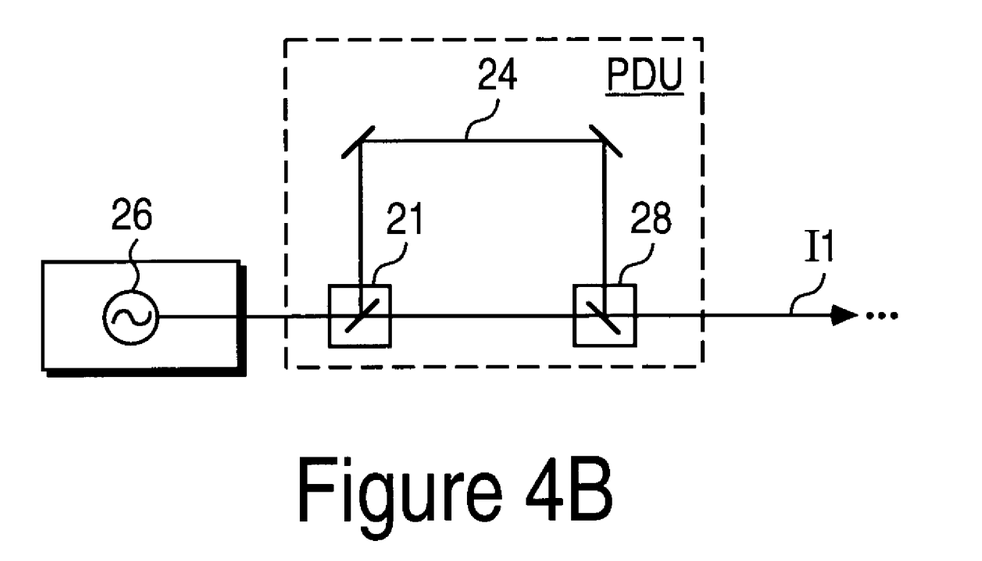

The polarization delay unit PDU is alternatively implemented using planar optical circuits, wherein the polarization maintaining fiber coupler 23 and the polarizing beam combiner 28 are implemented in planar optics and the delay element 24 is implemented using a planar optical waveguide. In yet another example, the polarization delay unit PDU is implemented using a polarization beam splitter 21, a free space optical path as the delay element 24, and a polarization beam combiner 28, as shown in FIG. 4B.

Figure 5A:
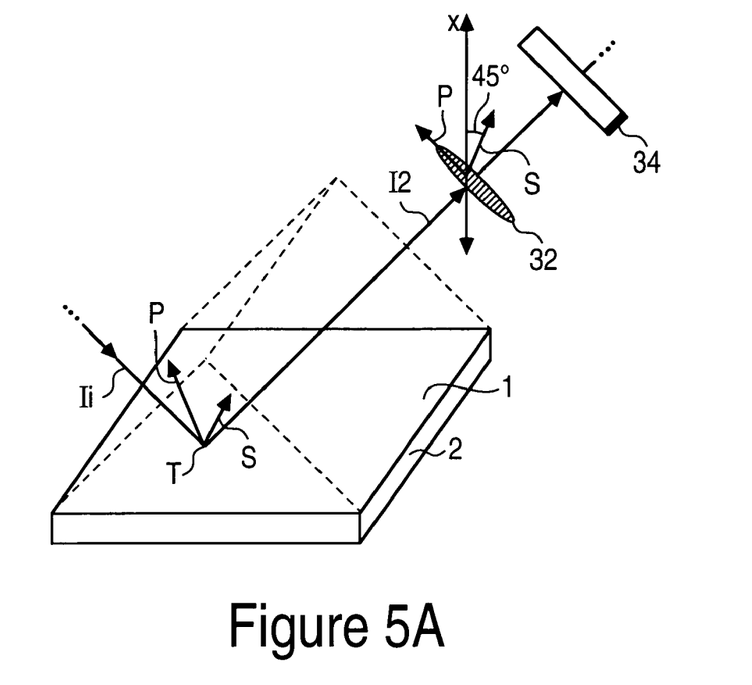
FIGS. 5A–5B show detailed views of the polarized optical signals included in the embodiments of the present invention.

A collimator 30 or other beam conditioning element is coupled to the tunable optical source 22, directing the optical signal $I_1$ to a target T on the conductive film 1 as shown in FIG. 5A. An optical signal 12 is reflected at the target T. The optical signal $I_2$ includes a pair of lightwaves $p_r$, $s_r$ having offset polarizations that correspond to the offset polarizations of the lightwave p and the lightwave s of the optical signal $I_1$. The lightwave p has an electric field component that is perpendicular to the plane of the conductive film 1, whereas the lightwave s has an electrical field that lies in the plane of the conductive film 1. The lightwave p couples to the surface plasmon, whereas the lightwave s does not couple to the surface plasmon. Accordingly, the lightwave $p_r$ of the optical signal $I_2$ undergoes a phase shift at the resonant wavelength $\lambda_R$ as indicated in FIG. 2, whereas a lightwave $S_r$ of the optical signal $I_2$ does not undergo such a phase shift.

The optical signal $I_2$ is received by a polarizer 32 having a polarization axis X that is rotationally offset from the polarization axes of the lightwaves $p_r$, $s_r$, by 45 degrees as shown in FIG. 5A. However, rotational offsets of the polarization axis X of the polarizer 32 from the polarization axes other than 45 degrees are also suitable.

The lightwaves $p_r$, $s_r$ of the optical signal $I_2$ interact as a result of passing through the polarizer 32 to form an interference signal I(t) at a detector 34. The interference signal I(t) is expressed in equation (1).

$$I(t)=E_S(t)^2+E_P(t)^2+2E_S E_P \cos(2\pi\gamma\tau t+\Delta\phi_{sp}) \qquad (1)$$

In equation (1), $E_S(t)$, $E_P(t)$ represent the magnitudes of the electrical fields of the lightwaves $p_r$, $s_r$, respectively, of the optical signal $I_2$; $\gamma$ is the rate at which the tunable optical source 22 is tuned or swept; $\tau$ is the relative delay induced between the lightwaves p, s of the optical signal $I_1$ provided by the tunable optical source 22; and $\Delta\phi_{sp}$ is the phase difference between the lightwaves $p_r$, $s_r$ of the optical signal $I_2$. Since the lightwave s of the optical signal $I_1$ does not couple to the surface plasmon, the lightwave $s_r$ of the optical signal $I_2$ does not experience a phase shift due to SPR. Thus, the phase difference $\Delta\phi_{sp}$ is the phase shift of the lightwave $p_r$, designated as the phase $\phi_p$. Because the lightwaves s, $s_r$ traverse the same optical path as the lightwaves p, $p_r$, determining the phase $\phi_p$ of the lightwave $p_r$ relative to the phase of the lightwave $s_r$ provides immunity to mechanical vibration, temperature variations, and other influences.

The interference signal I(t) is intercepted by the detector 34 as the wavelength $\lambda$ of the tunable optical source 22 is tuned over a wavelength range $\lambda_1$–$\lambda_2$ in the vicinity of the resonant wavelength $\lambda_R$. The detector 34 is responsive to the term $2E_S E_P \cos(2\pi\gamma\tau t +\phi_p)$ in the interference signal I(t), and can be filtered or otherwise tuned for responsiveness within a narrow bandwidth about the frequency $\gamma\tau$, to improve sensitivity with which the term $2E_s E_P \cos(2\pi\gamma\tau t+\phi_p)$ can be measured or detected. The detector 34 provides a detected signal $I_{DET}(t)=K_1 \cos(2\pi\gamma\tau t+\phi_p)$, where $K_1$ is a constant and where $\gamma\tau$ is the frequency difference, or beat frequency, between the lightwaves p, s of the optical signal $I_1$ provided by the tunable optical source 22. The detected signal $I_{DET}(t)$ is typically an electrical signal.

Typically, the detector 34 is a photodiode, photosensor or other suitable transducer for converting an intercepted optical signal into a corresponding electrical signal. Alternatively, the detector 34 is an array or a two-dimensional grid of detector elements $D_1$–$D_N$ that provide a series of electrical signals corresponding to a series of optical signals that are intercepted by each of the detector elements $D_1$–$D_N$.

Including a reference signal $I_{REF}$ in the optical phase detector 20 enables the phase $\phi_p$ in the term $2E_S E_P \cos(2\pi\gamma\tau t+\phi_p)$ of the interference signal I(t) to be isolated. For example, a reference signal $I_{REF}$ tapped from the optical signal $I_1$ via an optical coupler 37, reflected off a reference target $T_{REF}$, and passed through the polarizer 32, as shown in the embodiment of FIG. 4A, provides an interference signal $I_R(t)$ at a reference detector 34R that includes a term $E_{SREF}E_{PREF} \cos(2\pi\gamma\tau t)$. The reference detector 34R is responsive to the term $E_{SREF}E_{PREF} \cos(2\pi\gamma\tau t)$ in the interference signal $I_R(t)$ and provides frequency reference $I_{RDET}$ $(t)=K_2\cos(2\pi\gamma\tau t)$, where $K_2$ is a constant. The frequency reference $I_{RDET}(t)$ is typically an electrical signal.

The detected signal $I_{DET}(t)$ and the frequency reference $I_{RDET}(t)$ from the detectors 34, 34R are applied to an phase comparator, or other processor 36 to extract the phase $\phi_p$. Phase comparators suitable for extracting phase differences between applied signals are well know in the art, and are described, for example, in *Modern Electronic Circuits Reference Manual*, by Markus, John, McGraw-Hill, Inc., ISBN 0-07-040446-1, p. 699. However, any suitable processor 36 is used to extract or otherwise determine the phase $\phi_p$ from the detected signal $I_{DET}(t)$ and frequency reference $I_{RDET}(t)$.

FIG. 4A shows the reference optical signal $I_{REF}$ incident on the reference target $T_{REF}$ causing the reference optical signal $I_{REF}$ to traverse an optical path parallel to that traversed by the signals $I_1$, $I_2$. When the reference target $T_{REF}$ in the optical path of the reference signal $I_{REF}$ does not support excitation of a surface plasmon at the resonant wavelength $\lambda_R$, the reference signal $I_{REF}$ does not undergo a phase shift associated with SPR. The detected phase is then attributable to the refractive index of the dielectric 2 of the target T. When the reference target $T_{REF}$ in the optical path of the reference signal $I_{REF}$ supports excitation of a surface plasmon at the resonant wavelength $\lambda_R$, the reference signal $I_{REF}$ undergoes a phase shift associated with SPR. Here, the detected phase is a differential phase that is attributable to the difference between the refractive index of dielectric 2 of the target T and the refractive index of the dielectric of the reference target $T_{REF}$.

While exemplary schemes for providing the reference optical signal $I_{REF}$ have been presented, it is appreciated that any other suitable system, device, element or scheme is alternatively used to provide the reference optical signal $I_{REF}$ to isolate the phase $\phi_p$ induced by the SPR. The reference optical signal $I_{REF}$ provides the frequency reference $I_{RDET}(t)$ at the beat frequency $\gamma\tau$ of the interference signal I(t) as shown in FIG. 4A. In an alternative embodiment to that shown in FIG. 4A, the reference optical signal $I_{REF}$ is tapped from the optical signal $I_1$ and passed directly to the polarizer 32 and the detector 34, without reflection off of a reference target $T_{REF}$.

The wavelength $\lambda$ of the lightwave p of the optical signal $I_1$ is recorded in a memory or other storage device (not shown) as the phase $\phi_p$ is measured to establish a relationship between optical wavelength $\lambda$ and phase $\phi_p$ in the vicinity of the resonant wavelength $\lambda_R$. The wavelength $\lambda$ of the optical signal $I_1$ is recorded or determined using optical interferometry, homodyne or heterodyne spectral analysis as described in *Fiber Optic Test and Measurement*, edited by Dennis Derickson, ISBN 0-13-534330-5, pages 42–44, or using any other suitable wavelength discrimination technique. Alternatively, the wavelength $\lambda$ is determined based on a start wavelength $\lambda_1$ and start time $t_1$, stop wavelength $\lambda_2$ and stop time $t_2$, and the tuning rate $\gamma$ at which the tunable optical source 22 is tuned or swept between the start wavelength $\lambda_1$, and the stop wavelength $\lambda_2$ in the time interval $t_2-t_1$. For a tunable optical source 22 having a linear tuning characteristic over the wavelength range $\lambda_1-\lambda_2$, a direct mapping between time $t_X$ and wavelength $\lambda_X$ within the wavelength range $\lambda_1-\lambda_2$ is established. For example, within the tuning or sweep range of the tunable optical source 22, a wavelength $\lambda_X$ is determined based on corresponding times $t_X$ at which phase $\phi_p$ is measured according to the relationship $\lambda_X=\lambda_1+(t_X-t_1)\gamma$. When the tunable optical source 22 has non-linear tuning characteristics, those characteristics are used to map designated times within the sweeping or tuning of the tunable optical source 22 to wavelengths $\lambda_X$ within the wavelength range $\lambda_1-\lambda_2$. By recording the phase $\phi_p$ as a function of time as the tunable optical source 22 is tuned or swept and using the established mapping between times $t_X$ and wavelength $\lambda_X$ of the tunable optical source 22, phase $\phi_p$ versus wavelength $\lambda$ is determined.

From the relationship between wavelength $\lambda$ and phase $\phi_p$, the quantity $d\phi_p/d\lambda$ at the resonant wavelength $\lambda_R$ or sufficiently close to the resonant wavelength $\lambda_R$ can be readily determined, where the quantity $d\phi_p/d\lambda$ represents the sensitivity of the phase $\phi_p$ to changes in wavelength $\lambda$ at the resonant wavelength $\lambda_R$.

According to an alternative embodiment of the present invention, measurement of phase $\phi_p$ is used to approximate the quantity $d\phi_p/d\lambda$ at the resonant wavelength $\lambda_R$. FIG. 2 indicates that in the vicinity of the resonant wavelength, there is a wavelength range wherein the phase shift sensitivity to wavelength change, represented by the quantity $d\phi_p/d\lambda$ is approximately constant. Thus, the quantity $d\phi_p/d\lambda$ within this wavelength range provides an approximation of the quantity $d\phi_p/d\lambda$ at the resonant wavelength. The accuracy of this approximation depends on the uniformity of the slope of the phase $\phi_p$ versus wavelength $\lambda$ in the wavelength range within which the SPR phase transition occurs.

From the quantity $d\phi_p/d\lambda$ at the resonant wavelength $\lambda_R$, and a determination of the quantity $d\lambda/dn_S$, which represents the wavelength sensitivity to refractive index at the resonant wavelength $\lambda_R$, the quantity $d\phi_p/dn_s$, representing the sensitivity of phase $\phi_p$ to changes in refractive index $n_s$, is established as $d\phi_p/dn_s=(d\phi_p/d\lambda)(d\lambda/dn_s)$. The quantity $d\lambda/dn_s$ is determined in a variety of ways. In one example, the quantity $d\lambda/dn_s$ is determined from computer simulation of the configuration 10 of FIG. 1 using MATLAB or other suitable program or environment to solve the Fresnel reflections at the conductive film-dielectric interface to model the sensitivity of the resonant wavelength $\lambda_R$ to changes in refractive index $n_s$. In another example, the quantity $d\lambda/dn_s$ is determined empirically wherein targets T having dielectrics 2 with different known refractive indices $n_{S1}, n_{S2}...n_{SX}$ are illuminated sequentially or simultaneously by the optical signal $I_1$ at wavelengths $\lambda$ in the vicinity of the resonant wavelength $\lambda_R$ to determined the resonant wavelength $\lambda_{R1}$, $\lambda_{R2}...\lambda_{RX}$ of the SPR corresponding to each of the refractive indices $n_{S1}, n_{S2}...n_{SX}$. Curve-fitting of the resonant wavelengths $\lambda_{R1}, \lambda_{R2}...\lambda_{RX}$ to refractive indices $n_{S1}, n_{S2}...n_{SX}$, interpolation, or other suitable techniques are used to establish a mapping between refractive index $n_S$ and resonant wavelength $\lambda_R$ to determine the quantity $d\lambda/dn_S$ at the resonant wavelength $\lambda_R$.

The quantity $d\lambda/dn_S$ can also be determined by matching appropriate wave vectors at the interface between the conductive film 1 and the dielectric 2. This includes equating the wave vector $k_{SPR}=w/c\,((\epsilon_1 n_S^2)(\epsilon_1+n_S^2))^{1/2}$ of the surface plasmon to the wave vector $kx=n_4(2\pi/\lambda)\sin\phi_{SP}$ of the optical signal $I_1$, where $\epsilon_1$ is the dielectric constant of the conductive film 1, where $n_4$ is the refractive index of the prism 4, and where $\phi_{SP}$ is the angle of incidence of the optical signal $I_1$. The quantity $d\lambda/dn_S$ can be derived from the equation of the wave vectors $k_{SPR}$, kx, as equation (2), where the imaginary component of the dielectric constant $\epsilon_1$ of the conductive film 1 is set to zero.

$$\frac{d\lambda}{dn_S} = \frac{n_4 \varepsilon_1}{\frac{n_4 n_S^3}{\lambda}\left(\frac{1}{\varepsilon_1} - 1\right) + \frac{dn_4}{d\lambda} n_S(n_S^2 + \varepsilon_1)} \quad (2)$$

The alternatives presented for determining the quantity $d\lambda/dn_s$ at the resonant wavelength are exemplary. It is appreciated that any suitable scheme is alternatively used to determine or approximate the quantity $d\lambda/dn_S$ at the resonant wavelength $\lambda_R$, or at a wavelength suitably close to the resonant wavelength $\lambda_R$, so that the sensitivity of phase $\phi_p$ to changes in refractive index $n_s$ can be established as $d\phi_p/dn_s = (d\phi_p/d\lambda)(d\lambda/dn_s)$.

According to an alternative embodiment of the present invention, a mapping between phase $\phi_p$ and refractive index $n_S$ is established based on measuring phase $\phi_p$ for dielectrics 2 having different refractive indices $n_S$. In this embodiment, phase $\phi_p$ is detected and changes in refractive index $n_S$ of the dielectric 2 are determined from the established mapping. In one example, changes $dn_S$ in refractive index $n_S$ are related to shifts $d\phi_p$ in phase $\phi_p$ at the resonant wavelength $\lambda_R$ by a constant as provided for example, in *Immunosensor based on optical heterodyne phase detection*, Sensors and Actuators B, vol. 76, Xinglong Yu, et al., (2003), p. 200.

Figure 6:
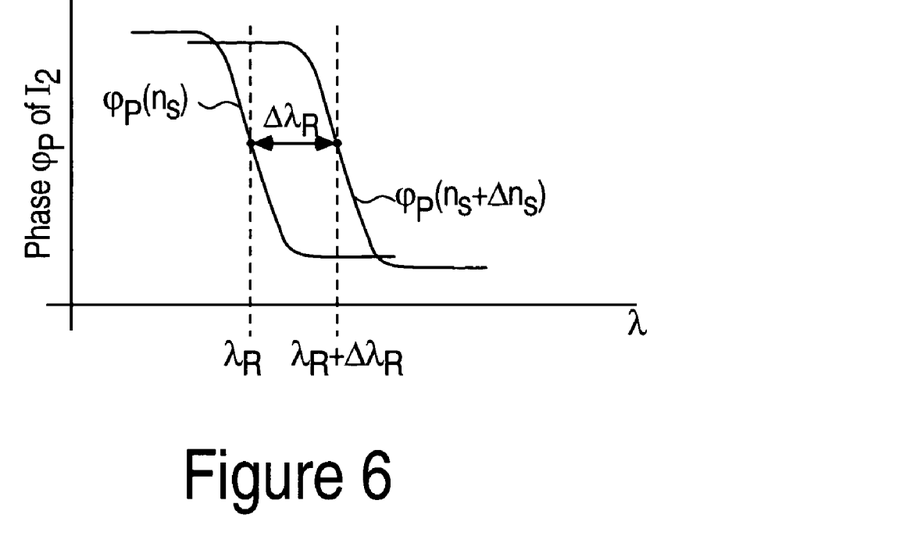
FIG. 6 shows exemplary phase contours versus optical wavelength according to embodiments of the present invention.

According to another embodiment of the present invention, the phase $\phi_p$ is detected versus wavelength $\lambda$ for two or more targets T with different refractive indices, for example, the refractive index $n_S$ and the refractive index $n_S + \Delta n_S$. The detected phases $\phi_p$ corresponding to the refractive indices $n_S$, $ns + \Delta n_S$, as shown in FIG. 6, are offset contours that result from shifts in resonant wavelength from the resonant wavelength $\lambda_R$ to the resonant wavelength $\lambda_R + \Delta \lambda_R$ due to the difference in refractive indices $\Delta n_S$. A mapping between resonant wavelength and refractive indices can then used to convert the difference in resonant wavelength $\Delta \lambda_R$ to a corresponding difference in refractive index $\Delta n_S$.

Figure 5B:
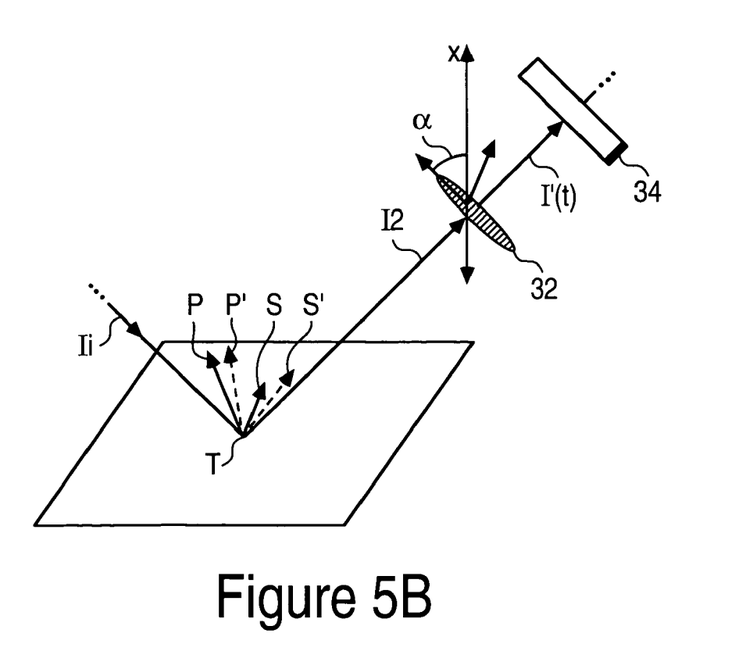
Figure 7:
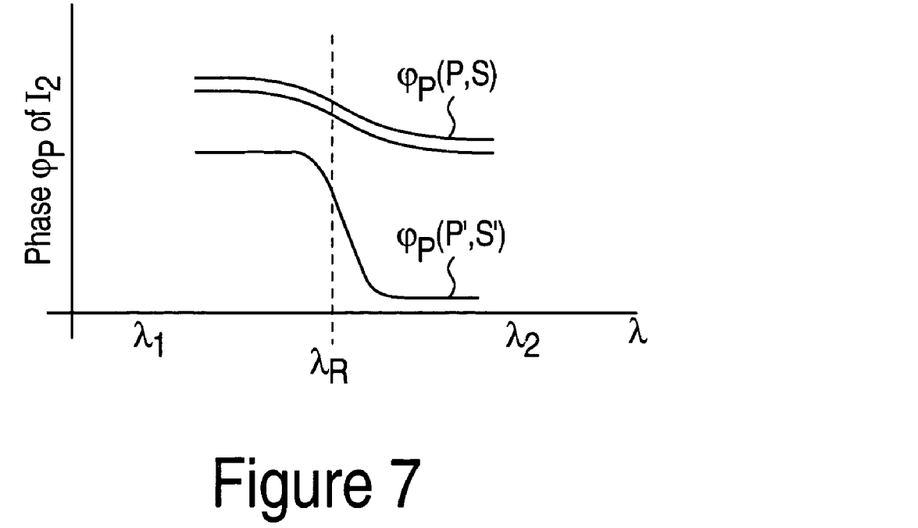
FIG. 7 shows phase transitions versus optical wavelength for different polarization alignments according to embodiments of the present invention.

In alternative embodiments of the present invention the sensitivity of changes in phase $\phi_p$ to changes in wavelength $\lambda$ in the vicinity of the resonant wavelength $\lambda_R$ is modified by misaligning, or rotating, the offset polarizations of the lightwaves p, s of the optical signal $I_1$ relative to the conventional polarizations p, s at the target T as shown in FIG. 5A, to result in lightwaves p', s' having misaligned polarizations p', s' as shown in FIG. 5B. Increases in this sensitivity, manifest as increases in the quantity $d\phi_p/d\lambda$, due to misalignment in polarizations provides corresponding increases in sensitivity of phase to changes in refractive index of the dielectric 2. FIG. 7 shows the phase $\phi_p$ (indicated as $\phi_p$(p',s')) of the optical signal $I_2$ when the optical signal $I_1$ has lightwaves p', s' that are misaligned relative to the lightwaves p,s. The phase of the optical signal $I_2$ when the optical signal $I_1$ has lightwaves p, s is indicated as $\phi_p$(p,s) in FIG. 7.

Misalignment of polarizations is achieved in a variety of alternative ways. For example, the misalignment is caused by creating a half-wavelength plate birefringence (not shown) in the fiber between the polarization beam combiner 28 and the collimator 30, for example in the embodiment shown in FIG. 4A. The misalignment is alternatively achieved by collimating the optical signal $I_1$ immediately after the polarization beam combiner 28, and interposing a slightly misaligned free-space half-wavelength plate in the beam of the collimated optical signal. Alternatively, the misalignment in polarization components can be achieved by a slight misalignment of the polarization beam combiner 28, with the collimator 30 being placed adjacent to the polarization beam combiner 28.

The sensitivity of changes in phase $\phi_p$ to changes in wavelength $\lambda$ in the vicinity of the resonant wavelength $\lambda_R$ can be increased or maximized empirically for a given misalignment of polarizations of the optical signal $I_1$, for example, by rotating the interposed half-wavelength plates when present, or by rotating the polarization beam combiner 28 while measuring phase $\phi_p$ as the optical wavelength $\lambda$ is swept or tuned in the vicinity of the resonant wavelength $\lambda_R$.

The sensitivity of changes in phase $\phi_p$ to changes in wavelength $\lambda$ in the vicinity of the resonant wavelength $\lambda_R$ can be increased or optimized based on an analytical determination of the polarization misalignment. In an analytical determination, the electric fields $E_{SO}$, $E_{PO}$ of the optical signal $I_2$ corresponding to the lightwaves $p_r$, $s_r$ are expressed by the matrix equation (3).

$$\begin{bmatrix} E_{SO} \\ E_{PO} \end{bmatrix} = \begin{bmatrix} r_S & 0 \\ 0 & r_P e^{j\phi p} \end{bmatrix} \begin{bmatrix} a & b \\ -b^* & a^* \end{bmatrix} \begin{bmatrix} E_S \\ E_P \end{bmatrix}$$

In the matrix equation (3), the term $r_s$ is a Jones matrix element for the reflection of the lightwave s at the target T; the term $r_p e^{i\phi p}$ is a Jones matrix element for the reflection of the lightwave p at the target T; the terms a and b are Jones matrix elements for the polarization misalignment where $a = |a|e^{i\delta a}$ and where $b = |b|e^{i\delta b}$; and the terms $E_S$, $E_P$ are the electric field components of the lightwaves p, s respectively of the optical signal $I_1$.

The reflected signal $I_2$ from the target T is passed through the polarizer 32 to provide an interference signal I'(t), as shown in FIG. 5B. The interference signal $I'(t) = |\cos\alpha\, E_{SO} + \sin\alpha\, E_{PO}|^2$ is intercepted by the detector 34, where the angle $\alpha$ represents the rotational offset between the lightwaves of the optical signal $I_2$ and the axis X of the polarizer 32. The detector 34 is responsive to the terms in the interference signal I'(t) in the vicinity of the frequency $\gamma\tau$, which is the frequency difference, or beat frequency, between the lightwaves p', s' of the optical signal $I_1$ provided by the tunable optical source 22. The detector 34 can be filtered or otherwise tuned for responsiveness within a narrow bandwidth about the frequency $\gamma\tau$, to improve sensitivity with which the designated terms in the interference signal I'(t) can be measured or detected. The detector 34 provides an electrical signal $I'_{DET}(t)$ that is represented in equation (4).

$I'_{DET}(t) = \cos^2\alpha |a||b| r_S^2 E_{SO} E_{PO} \cos(2\pi\gamma\tau t + \delta_a - \delta_b) + \cos\alpha \sin\alpha |a|^2 r_S r_P E_{SO} E_{PO} \cos(2\pi\gamma\tau t + 2\delta_a - \phi_p) - \cos\alpha \sin\alpha |b|^2 r_S r_P E_{SO} E_{PO} \cos(2\pi\gamma\tau t - 2\delta_b + \phi_p) - \sin^2\alpha |a||b| r_P^2 E_{SO} E_{PO} \cos(2\pi\gamma\tau t + \delta_a - \delta_b).$ (4).

High phase sensitivity versus wavelength is achieved based on the equation (4) for a misalignment of the polarizations of the optical signal $I_1$, wherein |b| is approximately equal to the reflectivity $r_P$ of the lightwave p from the target T, and wherein the sum of the phase $\phi_p$ of the SPR and the phases of the misalignments $\delta_a + \delta_b$ is an odd multiple of $\pi$. In a typical example, an increase in sensitivity is achieved for misalignments of less than 5 degrees between the polarizations of the lightwaves p, s and the polarizations of the lightwaves p', s'.

Figure 8A:
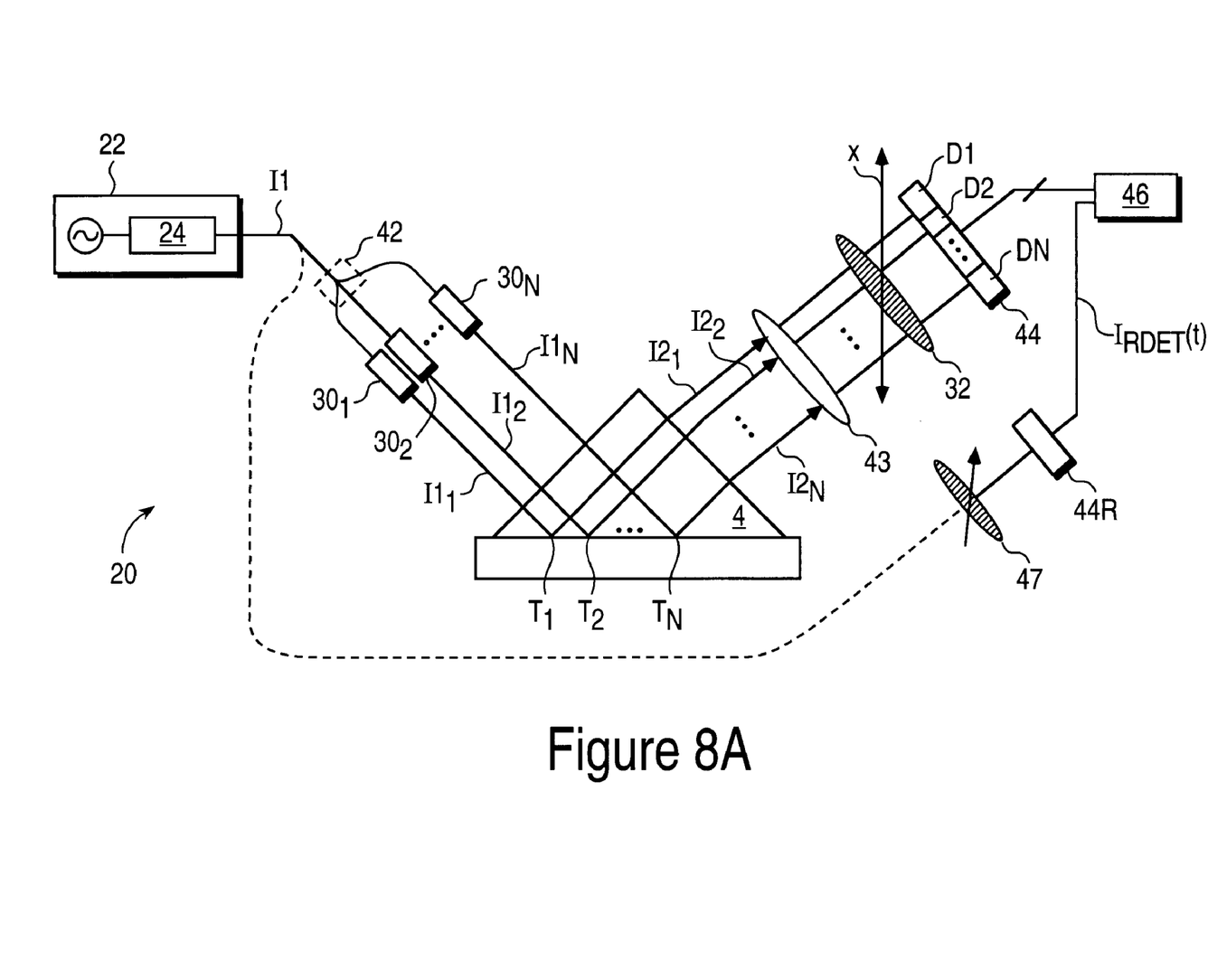
FIGS. 8A–8B show scaled optical phase detectors according to embodiments of the present invention.
Figure 8B:
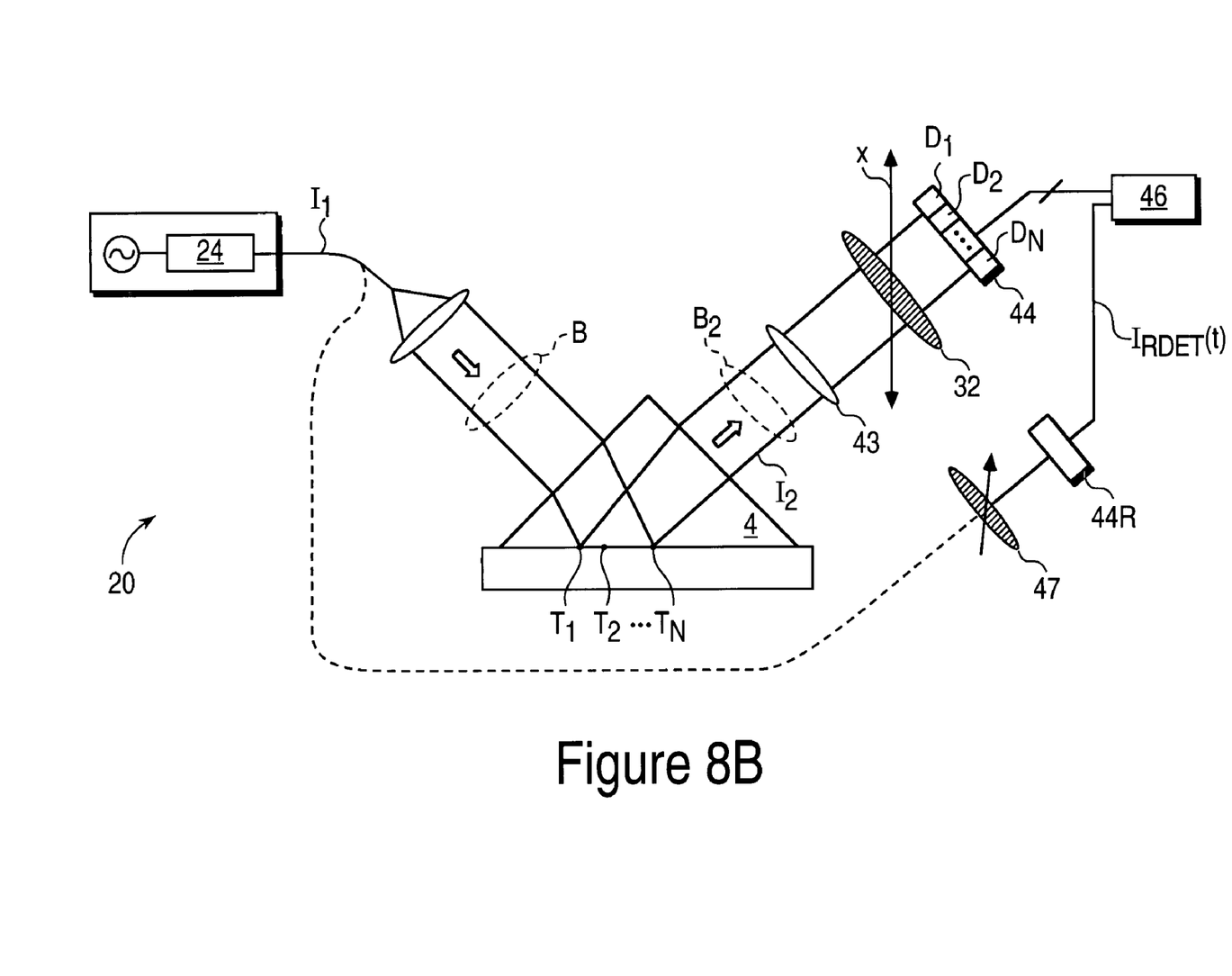

In alternative embodiments of the present invention shown in FIGS. 8A–8B, the optical phase detector 20 is scaled, enabling simultaneous or sequential detection of SPR-induced phase shifts from a target T that includes an array of SPR transducers, indicated as targets $T_1 - T_N$. In FIG.

8A, an array of targets $T_1$–$T_N$ are illuminated by optical signals $I1_1$–$I1_N$ provided from the optical signal $I_1$ by an optical splitter 42 and directed via collimators $30_1$–$30_N$. An imaging element 43, such as a lens is interposed between the array of targets $T_1$–$T_N$ and a detector 44 that includes an array of detector elements $D_1$–$D_N$. The imaging element 43 is positioned in the optical path between the array of targets $T_1$–$T_N$ and the polarizer 32 as shown, or between the polarizer 32 and the detector array 44. The imaging element 43 provides a map or other correspondence between the physical locations of the targets $T_1$–$T_N$ and physical locations of detector elements $D_1$–$D_N$ in the detector array 44, so that optical signals $I2_1$–$I2_N$ reflected from the array of targets $T_1$–$T_N$ are intercepted by corresponding detector elements $D_1$–$D_N$ in the detector array 44. The detector elements $D_1$–$D_N$ provide detected signals $I_{1DET}(t)$-$I_{NDET}(t)$ to a phase comparator or other processor 46. The processor 46 compares the detected signals $I_{1DET}(t)$-$I_{NDET}(t)$ to the frequency reference $I_{RDET}(t)$ to extract corresponding phases of the signals $I2_1$–$I2_N$ reflected from each of the targets within the array of targets $T_1$–$T_N$.

In the embodiment shown in FIG. 8A, the frequency reference $I_{RDET}(t)$ results from the reference optical signal $I_{REF}$ that is derived from the optical signal $I_1$ provided by the tunable optical source 22, via tapping of the optical signal $I_1$, polarizing the reference optical signal $I_{REF}$ via a polarizer 47 and detection of the resulting interference signal $I_R(t)$ via detector 44R. In an alternative embodiment, the frequency reference $I_{RDET}(t)$ is provided by a designated one of the detected signals $I_{1DET}(t)$-$I_{NDET}(t)$, for example the detected signal $I_{XDET}(t)$. The designated detected signal $I_{XDET}(t)$ corresponds to a target $T_X$ within the array of targets $T_1$–$T_N$. When the target $T_X$ does not induce an SPR phase shift at the wavelength of the optical signal $I1_X$ incident on the target $T_X$, phases extracted by the processor 46 are relative to the phase of the reference optical signal $I_{REF}$. When the target induces an SPR phase shift at the wavelength of the optical signal $I1_X$ incident on the target $T_X$, phases extracted by the processor 46 are differential. The differential phase corresponds to differential refractive indices between the targets in the array of targets, relative to the refractive index corresponding to the target $T_X$.

According to the embodiment of the present invention shown in FIG. 8B, a focusing element 47, such as a lens forms a beam B1 from the optical signal $I_1$ that is suitably wide to illuminate an array of targets $T_1$–$T_N$. The array of targets reflects the beam B1 of the optical signal $I_1$ to form a beam B2. The imaging element 43 positioned in the optical path between the array of targets $T_1$–$T_N$ and the polarizer 32 provides a correspondence between the physical locations of the targets $T_1$–$T_N$ and physical locations of detector elements $D_1$–$D_N$ in the detector array 44, so that portions of the beam B2 reflected from the corresponding targets positioned within the array of targets $T_1$–$T_N$ are intercepted by corresponding detector elements $D_1$–$D_N$ in the detector array 44. The detector elements $D_1$–$D_N$ provide detected signals $I_{1DET}(t)$-$I_{NDET}(t)$ to the phase comparator or other processor 46 that compares each of the detected signals $I_{1DET}(t)$-$I_{NDET}(t)$ to the frequency reference $I_{RDET}(t)$ to extract the phase of the optical signals within the beam B2 that are reflected from each of the targets within the array of targets $T_1$–$T_N$.

In the embodiment shown in FIG. 8B, the frequency reference $I_{RDET}(t)$ results from the reference optical signal $I_{REF}$ that is derived from the optical signal $I_1$ provided by the tunable optical source 22, via tapping of the optical signal $I_1$, polarizing the reference optical signal $I_{REF}$ via a polarizer 47 and detection of the resulting interference signal $I_R(t)$ via detector 44R. In an alternative embodiment, the frequency reference $I_{RDET}(t)$ is provided by a designated one of the detected signals $I_{1DET}(t)$-$I_{NDET}(t)$, for example the detected signal $I_{XDET}(t)$. The designated detected signal $I_{XDET}(t)$ corresponds to a target $T_X$ within the array of targets $T_1$–$T_N$. When the target $T_X$ does not induce an SPR phase shift at the wavelength of the portion of the optical beam B1 incident on the target $T_X$, phases extracted by the processor 46 are relative to the phase of the reference optical signal $I_{REF}$. When the target does induce an SPR phase shift at the wavelength of the optical signal $I1_X$ incident on the target $T_X$, phases extracted by the processor 46 are differential. The differential phase corresponds to differential refractive indices between the targets in the array of targets, relative to the refractive index corresponding to the target $T_X$.

Figure 9:
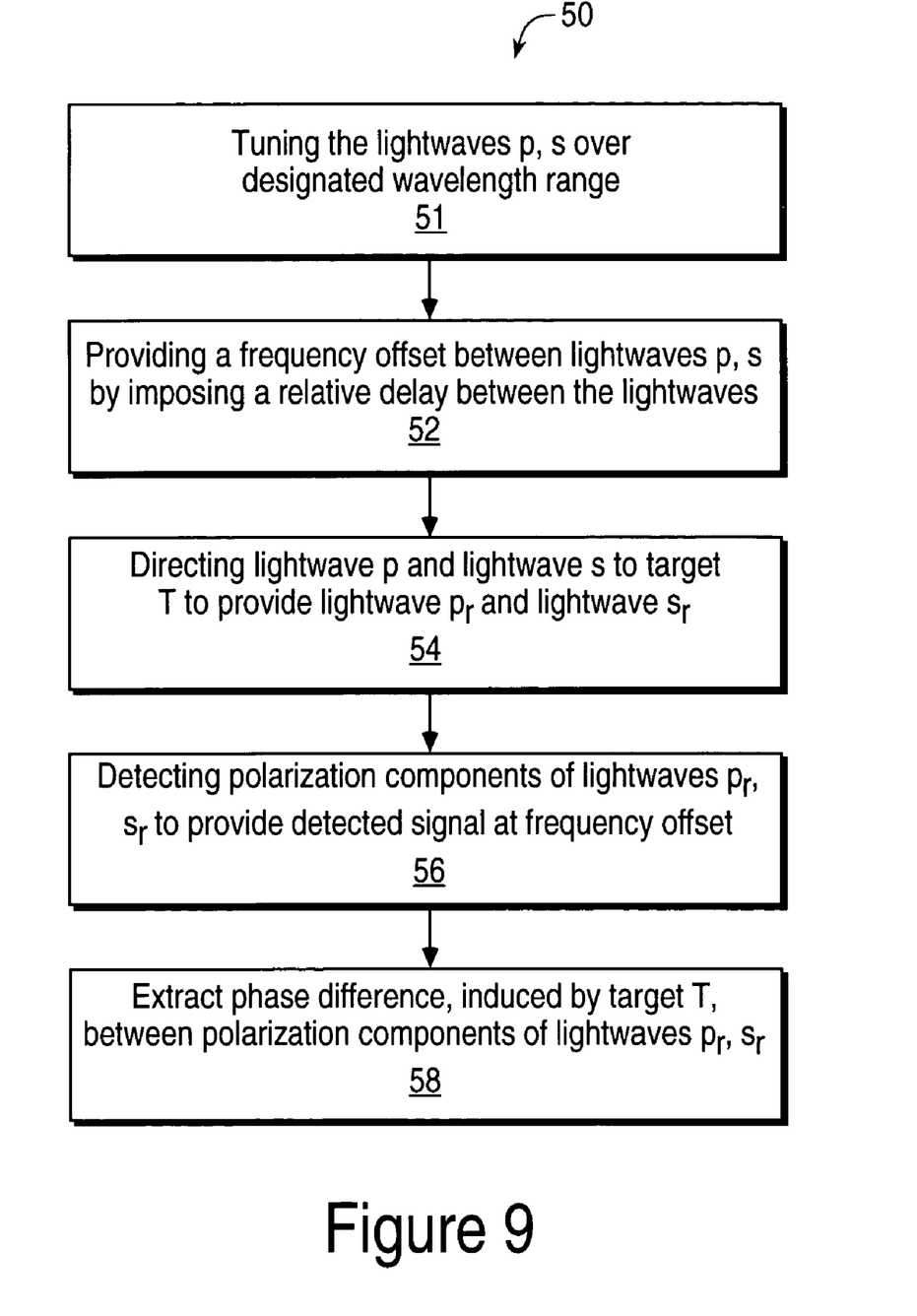
FIG. 9 shows a flow diagram of a phase detection method according to alternative embodiments of the present invention.

FIG. 9 shows a flow diagram of a phase detection method 50 in accordance with alternative embodiments of the present invention. In step 51 of the method 50, the lightwave p and the lightwave s are tuned over the wavelength range. In step 52, the frequency offset $\gamma\tau$ between the lightwave p and the lightwave s is provided as the wavelength of the optical signal $I_1$ is tuned, by imposing a relative delay $\tau$ between the lightwave p and the lightwave s. Step 54 includes directing the lightwave p and the lightwave s to the target T to provide the lightwave $p_r$ and the lightwave $s_r$ in response to the lightwave $p_r$ and the lightwave $s_r$. Step 56 includes detecting a polarization component of the lightwave $p_r$ and a polarization component of the lightwave $s_r$ to provide the detected signal at the frequency offset $\gamma\tau$. In step 58, the phase difference, or phase $\phi_p$, induced by the target T, between the polarization components of the lightwaves p, s, is extracted. Extracting the phase $\phi_p$ typically includes phase comparing the detected signal to the frequency reference at the frequency offset $\gamma\tau$. In one example, the frequency reference is derived from detecting the reference optical signal that passes through a polarizer, where the reference optical signal is tapped from the lightwaves p, s of the optical signal $I_1$.

While an SPR transducer 10, or array of SPR transducers have been used as exemplary target T according to the embodiments of the present invention, the target T is alternatively any device, element, or system suitable for providing an optical signal $I_2$ in response to an applied optical signal $I_1$, where the optical signal $I_2$ results from reflection, transmission or other processing of the optical signal $I_1$. response to an applied optical signal $I_1$, where the optical signal $I_2$ results from reflection, transmission or other processing of the optical signal $I_1$.

While the embodiments of the present invention have been illustrated in detail, it should be apparent that modifications and adaptations to these embodiments may occur to one skilled in the art without departing from the scope of the present invention as set forth in the following claims.

The invention claimed is:
1. An optical phase detector, comprising:
   a tunable optical source generating a first lightwave having a first polarization and a second lightwave having a second polarization and a delay relative to the first lightwave, the delay inducing a frequency offset between the first lightwave and the second lightwave as the tunable optical source is tuned over a designated wavelength range;
   a target, receiving the first lightwave and the second lightwave, providing a third lightwave and a fourth lightwave in response to the first lightwave and the second lightwave;

a detector, intercepting a polarization component of the third lightwave and a polarization component of the fourth lightwave, and providing a detected signal at the frequency offset; and a processor receiving the detected signal and extracting a phase difference, induced by the target, between the third lightwave and the fourth lightwave.

2. The optical phase detector of claim 1 wherein extracting the phase difference between the third lightwave and the fourth lightwave includes phase comparing the detected signal to a frequency reference at the frequency offset.

3. The optical phase detector of claim 2 wherein the frequency reference is provided by tapping the first lightwave and the second lightwave from the tunable optical source, passing the tapped first lightwave and tapped second lightwave through a polarizer and detecting a resulting signal from the polarizer at the frequency offset between the tapped first lightwave and the tapped second lightwave.

4. The optical phase detector of claim 3 wherein the tapped first lightwave and the tapped second lightwave are reflected at a reference target prior to the passing through the polarizer.

5. The optical phase detector of claim 1 wherein the first lightwave has an s polarization and the second lightwave has an orthogonal p polarization.

6. The optical phase detector of claim 4 wherein the phase difference is the phase of the p polarization component.

7. The optical phase detector of claim 1 wherein the target includes an SPR transducer.

8. The optical phase detector of claim 1 further comprising an imaging element interposed between the target and detector, the imaging element mapping physical locations of the target to physical locations of the detector.

9. The optical phase detector of claim 8 wherein the target includes an array of SPR transducers.

10. The optical phase detector of claim 1 wherein the tunable optical source includes a tunable laser coupled to a polarization maintaining coupler, an optical delay element coupled to a first output of the polarization maintaining coupler, a polarizing beam combiner coupled between the optical delay element and a second output of the polarization maintaining coupler, wherein the polarizing beam combiner is coupled to a collimator.

11. The optical phase detector of claim 1 wherein the frequency offset is established by the relative delay and a tuning rate of the tunable optical source.

12. An optical phase detection method, comprising:

tuning, over a designated wavelength range, a first lightwave having a first polarization and a second lightwave having a second polarization offset from the first polarization;

providing a frequency offset between the first lightwave and the second lightwave by imposing a relative delay between the first lightwave and the second lightwave;

directing the first lightwave and the second lightwave to a target providing a third lightwave and a fourth lightwave in response to the first lightwave and the second lightwave;

detecting a polarization component of the third lightwave and a polarization component of the fourth lightwave, to provide a detected signal at the frequency offset; and extracting a phase difference, induced by the target, between the polarization component of the third lightwave and the polarization component of the fourth lightwave.

13. The method of claim 12 wherein extracting the phase difference includes phase comparing the detected signal to a frequency reference at the frequency offset.

14. The method of claim 12 wherein the first lightwave has an s polarization and the second lightwave has an orthogonal p polarization.

15. The method of claim 12 wherein the frequency reference is derived from detecting a reference optical signal that passes through a polarizer, the reference optical signal including a tapping of the first lightwave and a tapping of the second lightwave.

16. The method of claim 14 wherein the phase difference is the phase of the p polarization component.

17. The method of claim 16 wherein the phase is recorded versus wavelength within the designated wavelength range.

18. The method of claim 12 wherein the target includes a SPR transducer.

19. The method of claim 13 further comprising mapping physical locations of the target to physical locations of a detector.

20. The method of claim 19 wherein the target includes an array of SPR transducers.

* * * * *